United States Patent
Wang et al.

(10) Patent No.: US 9,125,607 B2
(45) Date of Patent: *Sep. 8, 2015

(54) REAL-TIME SELF-CALIBRATING SENSOR SYSTEM AND METHOD

(75) Inventors: Lu Wang, Pasadena, CA (US); Rajiv Shah, Rancho Palos Verdes, CA (US); Wayne A. Morgan, Northridge, CA (US); Barry Keenan, Sherman Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 816 days.

This patent is subject to a terminal disclaimer.

(21) Appl. No.: 13/340,562

(22) Filed: Dec. 29, 2011

(65) Prior Publication Data

US 2012/0123690 A1 May 17, 2012

Related U.S. Application Data

(63) Continuation of application No. 12/826,497, filed on Jun. 29, 2010, now Pat. No. 8,249,683, which is a continuation of application No. 11/323,216, filed on Dec. 30, 2005, now Pat. No. 7,774,038.

(51) Int. Cl.
*A61B 5/1473* (2006.01)
*A61B 5/1468* (2006.01)
(Continued)

(52) U.S. Cl.
CPC ............. *A61B 5/1495* (2013.01); *A61B 5/1468* (2013.01); *A61B 5/1473* (2013.01);
(Continued)

(58) Field of Classification Search
CPC ................... A61B 2560/0223; A61B 5/0031; A61B 5/14532; A61B 5/1495; A61B 5/145; A61B 5/14865; A61B 5/14503; A61B 5/1473; A61B 5/1468; A61B 5/1486; A61M 2005/1726

See application file for complete search history.

(56) References Cited

U.S. PATENT DOCUMENTS 4,168,212 A 9/1979 Faktor et al.
4,433,072 A 2/1984 Pusineri et al.
(Continued)

FOREIGN PATENT DOCUMENTS

EP 0 017 731 A1 10/1980
EP 0 472 057 A2 2/1992
(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.
(Continued)

*Primary Examiner* — Navin Natnithithadha
(74) *Attorney, Agent, or Firm* — Pillsbury Winthrop Shaw Pittman LLP

(57) ABSTRACT

A system and method for calibrating a sensor of a characteristic monitoring system in real time utilizes a self-calibration module for periodic determination of, and compensation for, the IR drop across unwanted resistances in a cell. A current-interrupt switch is used to open the self-calibration module circuit and either measure the IR drop using a high-frequency (MHz) ADC module, or estimate it through linear regression of acquired samples of the voltage across the sensor's working and reference electrodes (Vmeasured) over time. The IR drop is then subtracted from the closed-circuit value of Vmeasured to calculate the overpotential that exists in the cell (Vimportant). Vimportant may be further optimized by subtracting the value of the open-circuit voltage (Voc) across the sensor's working and reference electrodes. The values of Vmeasured and Vimportant are then controlled by respective first and second control units to compensate for the IR drop.

42 Claims, 9 Drawing Sheets

(51) Int. Cl.
    *A61B 5/1495*    (2006.01)
    *A61B 5/1486*    (2006.01)
    *A61B 5/00*    (2006.01)
    *A61B 5/145*    (2006.01)
    *A61M 5/172*    (2006.01)

(52) U.S. Cl.
    CPC ........... *A61B5/14865* (2013.01); *A61B 5/0031* (2013.01); *A61B 5/14532* (2013.01); *A61B 2560/0223* (2013.01); *A61M 2005/1726* (2013.01)

(56) References Cited

U.S. PATENT DOCUMENTS

| | | | |
|---|---|---|---|
| 4,494,950 A | 1/1985 | Fischell | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,703,756 A | 11/1987 | Gough et al. | |
| 4,731,726 A | 3/1988 | Allen, III | |
| 4,781,798 A | 11/1988 | Gough | |
| 4,871,351 A | 10/1989 | Feingold | |
| 5,080,653 A | 1/1992 | Voss et al. | |
| 5,097,122 A | 3/1992 | Colman et al. | |
| 5,101,814 A | 4/1992 | Palti | |
| 5,108,819 A | 4/1992 | Heller et al. | |
| 5,165,407 A | 11/1992 | Wilson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,266,179 A * | 11/1993 | Nankai et al. | 204/401 |
| 5,282,950 A | 2/1994 | Dietze et al. | |
| 5,284,140 A | 2/1994 | Allen et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,356,786 A | 10/1994 | Heller et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,497,772 A | 3/1996 | Schulman et al. | |
| 5,543,326 A | 8/1996 | Heller et al. | |
| 5,569,186 A | 10/1996 | Lord et al. | |
| 5,586,553 A | 12/1996 | Halili et al. | |
| 5,593,852 A | 1/1997 | Heller et al. | |
| 5,660,163 A | 8/1997 | Schulman et al. | |
| 5,665,065 A | 9/1997 | Colman et al. | |
| 5,665,222 A | 9/1997 | Heller et al. | |
| 5,750,926 A | 5/1998 | Schulman et al. | |
| 5,779,665 A | 7/1998 | Mastrototaro et al. | |
| 5,791,344 A | 8/1998 | Schulman et al. | |
| 5,800,420 A | 9/1998 | Gross et al. | |
| 5,807,375 A | 9/1998 | Gross et al. | |
| 5,820,622 A | 10/1998 | Gross et al. | |
| 5,904,708 A | 5/1999 | Goedeke | |
| 5,917,346 A | 6/1999 | Gord et al. | |
| 5,965,380 A | 10/1999 | Heller et al. | |
| 5,972,199 A | 10/1999 | Heller et al. | |
| 5,999,848 A | 12/1999 | Gord et al. | |
| 5,999,849 A | 12/1999 | Gord et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,193,873 B1 * | 2/2001 | Ohara et al. | 205/792 |
| 6,259,937 B1 | 7/2001 | Schulman et al. | |
| 6,275,717 B1 | 8/2001 | Gross et al. | |
| 6,329,161 B1 | 12/2001 | Heller et al. | |
| 6,428,684 B1 | 8/2002 | Warburton | |
| 6,472,122 B1 | 10/2002 | Schulman et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,554,798 B1 | 4/2003 | Mann et al. | |
| 6,558,320 B1 | 5/2003 | Causey, III et al. | |
| 6,560,471 B1 | 5/2003 | Heller et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,654,625 B1 | 11/2003 | Say et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,733,471 B1 | 5/2004 | Ericson et al. | |
| 6,746,582 B2 | 6/2004 | Heller et al. | |
| 6,749,740 B2 | 6/2004 | Liamos et al. | |
| 6,809,507 B2 | 10/2004 | Morgan et al. | |
| 6,809,653 B1 | 10/2004 | Mann et al. | |
| 6,881,551 B2 | 4/2005 | Heller et al. | |
| 6,893,545 B2 | 5/2005 | Gotoh et al. | |
| 6,916,159 B2 | 7/2005 | Rush et al. | |
| 6,932,894 B2 | 8/2005 | Mao et al. | |
| 6,942,518 B2 | 9/2005 | Liamos et al. | |
| 6,952,604 B2 | 10/2005 | DeNuzzio et al. | |
| 7,125,382 B2 | 10/2006 | Zhou et al. | |
| 7,241,266 B2 | 7/2007 | Zhou et al. | |
| 7,267,665 B2 | 9/2007 | Steil et al. | |
| 7,426,408 B2 | 9/2008 | DeNuzzio et al. | |
| 7,525,298 B2 | 4/2009 | Morgan et al. | |
| 7,774,038 B2 | 8/2010 | Wang et al. | |
| 7,935,057 B2 * | 5/2011 | Goode et al. | 600/365 |
| 7,985,330 B2 * | 7/2011 | Wang et al. | 205/792 |
| 7,998,071 B2 * | 8/2011 | Goode et al. | 600/365 |
| 8,005,525 B2 * | 8/2011 | Goode et al. | 600/347 |
| 8,010,174 B2 * | 8/2011 | Goode et al. | 600/347 |
| 8,114,268 B2 * | 2/2012 | Wang et al. | 205/792 |
| 8,114,269 B2 * | 2/2012 | Cooper et al. | 205/792 |
| 8,249,683 B2 * | 8/2012 | Wang et al. | 600/345 |
| 8,532,732 B2 * | 9/2013 | Shah et al. | 600/345 |
| 8,591,416 B2 * | 11/2013 | Shah et al. | 600/309 |
| 8,602,992 B2 * | 12/2013 | Shah et al. | 600/309 |
| 8,608,924 B2 * | 12/2013 | Cooper et al. | 204/406 |
| 2002/0082665 A1 | 6/2002 | Haller et al. | |
| 2002/0161288 A1 | 10/2002 | Shin et al. | |
| 2003/0078560 A1 | 4/2003 | Miller et al. | |
| 2003/0088166 A1 | 5/2003 | Say et al. | |
| 2003/0130616 A1 | 7/2003 | Steil et al. | |
| 2003/0152823 A1 | 8/2003 | Heller et al. | |
| 2003/0168338 A1 | 9/2003 | Gao et al. | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0074785 A1 | 4/2004 | Holker et al. | |
| 2004/0093167 A1 | 5/2004 | Braig et al. | |
| 2004/0111017 A1 | 6/2004 | Say et al. | |
| 2004/0118704 A1 | 6/2004 | Wang et al. | |

(56) References Cited

U.S. PATENT DOCUMENTS

| | | | |
|---|---|---|---|
| 2004/0220517 A1* | 11/2004 | Starkweather et al. | 604/67 |
| 2005/0043598 A1 | 2/2005 | Goode, Jr. et al. | |
| 2005/0164286 A1 | 7/2005 | O'uchi et al. | |
| 2005/0214585 A1 | 9/2005 | Li et al. | |
| 2005/0244811 A1 | 11/2005 | Soundarrajan et al. | |
| 2005/0265094 A1 | 12/2005 | Harding et al. | |
| 2006/0086623 A1 | 4/2006 | Narula et al. | |
| 2007/0163894 A1* | 7/2007 | Wang et al. | 205/792 |
| 2007/0169533 A1 | 7/2007 | Shah et al. | |
| 2007/0170073 A1 | 7/2007 | Wang et al. | |
| 2007/0173712 A1 | 7/2007 | Shah et al. | |
| 2007/0236224 A1 | 10/2007 | Augustyniak et al. | |
| 2010/0324853 A1* | 12/2010 | Wang et al. | 702/104 |
| 2012/0310063 A1* | 12/2012 | Wang et al. | 600/347 |

FOREIGN PATENT DOCUMENTS

| | | |
|---|---|---|
| EP | 1338295 A1 | 8/2003 |
| GB | 2 288 875 A | 11/1995 |
| IE | 970443 | 12/1998 |
| JP | 2002-505008 | 2/2002 |
| JP | 2005-030955 | 2/2005 |
| WO | WO 90/12315 | 10/1990 |
| WO | WO 96/37246 A1 | 11/1996 |
| WO | WO 00/49941 | 8/2000 |
| WO | WO 00/68676 | 11/2000 |
| WO | WO 02/058537 A2 | 8/2002 |
| WO | WO 03/036310 A1 | 5/2003 |
| WO | WO 2004/060455 A1 | 7/2004 |

OTHER PUBLICATIONS

Abel et al., "A Method for Evaluating in vivo the Functional Characteristics of Glucose Sensors," Biosensors, 1986, pp. 211-220, vol. 2.
Boguslavsky et al., "Applications of redox polymers in biosensors," Solid State Ionics, 1993, pp. 189-197, vol. 60.
Geise et al., "Electropolymerized 1,3-diaminobenzene for the construction of a 1-1'-dimethylferrocene mediated glucose biosensor," Analytica Chim. Acta.,1993, pp. 467-473, v18.
Gernet et al., "A planar glucose enzyme electrode," Sensors and Actuators, 1989, pp. 537-540, vol. 17, Elsevier Sequoia, Netherlands.
Gernet et al., "Fabrication and Characterization of a Planar Electrochemical Cell and its Application as a Glucose Sensor," Sensors and Actuators, 1989, pp. 49-70, vol. 18.
Gorton et al., "Amperometric glucose senosrs based on immobilized glucose-oxidizing enzymes and chemically modified electrodes," Analytica Chim Acta., 1991, pp. 43-54, v. 249.
Gorton et al., "Amperometric biosensors based on an apparent direct electron transfer between electrodes and immobilized peroxidases," Analyst, 1992, pp. 1235-1241, vol. 117.
Gough et al., "Two-Dimensional Enzyme Electrode Sensor for Glucose," Analytical Chemistry, 1985, pp. 2351-2357, vol. 57.
Gregg et al., "Redox polymer films containing enzymes," J. Phys. Chem., 1991, pp. 5970-5975.
Gregg et al., "Cross-Linked Redox Gels Containing Glucose Oxidase for Amperometric Biosensor Applications," Anal. Chem., 1990, pp. 258-263, vol. 62.
Heller et al., "Electrical Wiring of Redox Enzymes," Accounts of Chemical Research, 1990, pp. 128-134, vol. 23, No. 5.
Johnson et al., "In vivo evaluation of an electroenzymatic glucose sensor implanted in subcutaneous tissue," Biosensors & Bioelectronics, 1992, pp. 709-714, vol. 7.
Jonsson et al., "An Electrochemical Sensor for Hydrogen Peroxide Based on Peroxidase Adsorbed on a Spectrographic Graphite Electrode," Electroanalysts, 1989, pp. 465-468, v. 1.
Kanapieniene et al., "Miniature glucose biosensor with extended linearity," Sensors and Actuators, 1992, pp. 37-40, vol. B, No. 10.
Kawamori et al., "Perfect Normalization of Excessive Glucagon Responses to Intravenous Arginine in Human Diabetes Mellitus With . . . ," Diabetes, 1980, pp. 762-765, vol. 29.
Kimura et al., "An immobilized Enzyme Membrane Fabrication Method using an Ink Jet Nozzle," Biosensors, 1988, pp. 41-52, vol. 4.
Koudelka et al., "In-vivo Behaviour of Hypodermically Implanted Microfabricated Glucose Sensors," Biosensors & Bioelectronics, 1991, pp. 31-36, vol. 6.
Mastrototaro et al., "An electroenzymatic glucose sensor fabricated on a flexible substrate," Sensors and Actuators, 1991, pp. 139-144, vol. 5.
Mastrototaro et al., "An Electroenzymatic Sensor Capable of 72 Hour Continuous Monitoring of Subcutaneous Glucose," 14th Int'l Diabetes Federation Congress, 1991.
McKean et al., "A Telemetry-Instrumentation System for Chronically Implanted Glucose and Oxygen Sensors," IEEE Transactions on Biomedical Eng., 1988, pp. 526-532, vol. 35, No. 7.
Monroe, "Novel implantable glucose sensors," ACL, 1989, pp. 8-16.
Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.
Nakamato et al., "A Lift-Off Method for Patterning Enzyme-Immobilized Membranes in Multi-Biosensors," Sensors and Actuators, 1988, pp. 165-172, vol. 13.
Nishida et al., "Clinical applications of the wearable artificial endocrine pancreas with the newly designed . . . ," Path. and Treat. of NIDDM . . . , 1994, p. 353-358, No. 1057.
Shichiri et al., "An artificial endocrine pancreas—problems awaiting solutions for long term clinical applications of . . . ," Frontiers Med. Biol. Eng., 1991, pp. 283-292, v.3.
Shichiri et al., "Wearable Artificial Endocrine Pancreas with Needle-Type Glucose Sensor," The Lancet, 1982, pp. 1129-1131, vol. 2 (8308).
Shichiri et al., "Telemetry Glucose Monitoring Device with Needle-Type Glucose Sensor," Diabetes Care, May-Jun. 1986, pp. 298-301, vol. 9, No. 3.
Shichiri et al., "Normalization of the Paradoxic Secretion of Glucagen in Diabetics Who Were Controlled by the Artificial Beta Cell," Diabetes, 1979, pp. 272-275, vol. 28.
Shichiri et al., "Closed-Loop Glycemic Control with a Wearable Artificial Endocrine Pancreas," Diabetes, 1984, pp. 1200-1202, vol. 33.
Shichiri et al., "In Vivo Characteristics of Needle-Type Glucose Sensor," Hormone and Metabolic Research, 1988, pp. 17-20, vol. 20.
Shichiri et al., "A Needle-Type Glucose Sensor," Life Support Systems: The Journal of the European Society for Artificial Organs, 1984, pp. 7-9, vol. 2, supplement 1.
Shichiri et al., "The Wearable Artificial Endocrine Pancreas with a Needle-Type Glucose Sensor," Acta Pediatr, Jpn, 1984, pp. 358-370, vol. 26.
Shichiri et al., "Glycaemic Control in Pancreatectomized Dogs with a Wearable Artificial Endocrine Pancreas," Diabetologica, 1983, pp. 179-184, vol. 24.
Shichiri et al., "Membrane design for extending the long-life of an implantable glucose sensor," Diab. Nutr. Metab., 1989, pp. 309-313, vol. 2.
Shinkai et al., "Molecular Recognition of Mono- and Di-Saccharides by Phenylboronic Acids in Solvent Extraction and as a Monolayer," J. Chem. Soc., 1991, pp. 1039-1041.
Tamiya et al., "Micro Glucose Sensors Using Electron Mediators Immobilized on a Polypyrrole-Modified Electrode," Sensors and Actuators, 1989, pp. 297-307, v.18.
Tsukagoshi et al., "Specific Complexation with Mono- and Disaccharides That Can Be Detected by Circular Dichroism," J. Org. Chem., 1991, pp. 4089-4091, vol. 56.
Urban et al., "Minaturized multi-enzyme biosensors integrated with pH sensors on flexible polymer carriers . . . ," Biosensors & Bioelectronics, 1992, pp. 733-739, vol. 7.
Urban et al., "Miniaturized thin-film biosensors using covalently immobilized glucose oxidase," Biosensors & Bioelectronics, 1991, pp. 555-562, vol. 6.
Velho et al., "In vivo calibration of a subcutaneous glucose sensor for determination of subcutaneous glucose kinetics," Diab. Nutr. Metab., 1988 pp. 227-233, v.3.
Yokoyama et al., "Integrated Biosensor for Glucose and Galactose," Analytica Chimica Acta., 1989, pp. 137-142, vol. 218.

(56) References Cited

OTHER PUBLICATIONS

Nishida et al., "Development of a ferrocene-mediated needle-type glucose sensor . . . ," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinica Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n. 5.

Jobst et al., "Thin-Film Microbiosensors for Glucose-Lactate Monitoring," Anal. Chem., 1996, p. 3173-3179, vol. 68.

Shults et al., "A Telemetry-Instrumentation System for Monitoring Multiple Subcutaneously Implanted Glucose Sensors," IEEE Trans. on Biomed. Eng., 1994, pp. 937-42, v41, n. 10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-2077, vol. 65.

Bindra et al., "Design and In Vitro Studies of a Needle-Type Glucose Sensor for Subcutaneous Monitoring," Anal. Chem., 1991, pp. 1692-1696, vol. 63.

PCT: International Search Report (PCT/US2006/049015; dated Mar. 3, 2008; 4-pgs.).

Hickling A: Studies in electrode polarisation. Part IV. The automatic control of the potential of a working electrode:, Transactions of the Faraday Society, Butterworths Scientific Publications Ltd., London, GB, vol. 38, Jan. 1, 1942, pp. 27-33, XP008149119.

* cited by examiner

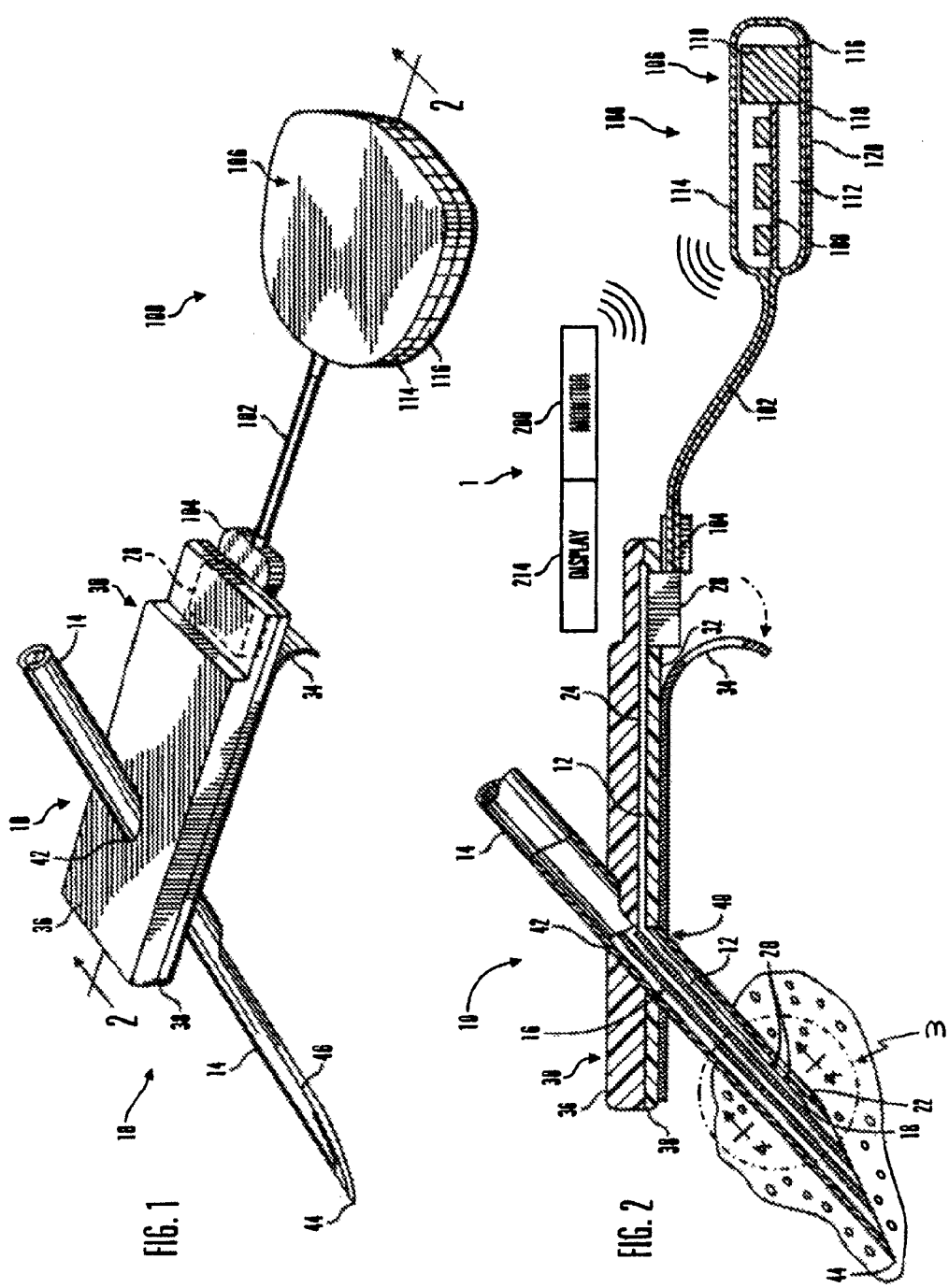

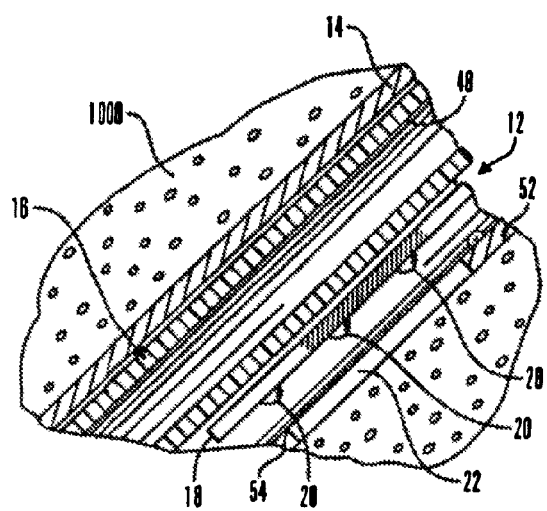
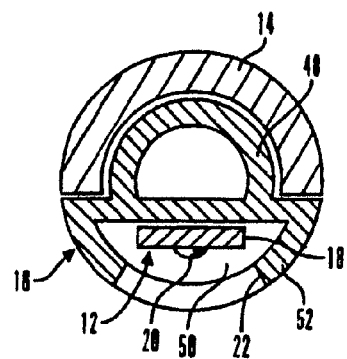
FIG. 3
FIG. 4

REAL-TIME SELF-CALIBRATING SENSOR SYSTEM AND METHOD

RELATED APPLICATION DATA

This is a continuation of application Ser. No. 12/826,497, filed Jun. 29, 2010, which is a continuation of application Ser. No. 11/323,216, filed Dec. 30, 2005, now U.S. Pat. No. 7,774,038.

FIELD OF THE INVENTION

This invention relates generally to subcutaneous and implantable sensor devices and, in particular embodiments, to methods and systems for providing real-time self-calibrating sensor devices.

BACKGROUND OF THE INVENTION

Over the years, a variety of electrochemical sensors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient.

Generally, small and flexible electrochemical sensors can be used to obtain periodic readings over an extended period of time. In one form, flexible subcutaneous sensors are constructed in accordance with thin film mask techniques in which an elongated sensor includes thin film conductive elements encased between flexible insulative layers of polyimide sheets or similar material. Such thin film sensors typically include a plurality of exposed electrodes at one end for subcutaneous placement with a user's interstitial fluid, blood, or the like, and a corresponding exposed plurality of conductive contacts at another end for convenient external electrical connection with a suitable monitoring device through a wire or cable. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571.

These electrochemical sensors have been applied in a telemetered characteristic monitor system. As described, e.g., in commonly-assigned U.S. Pat. No. 6,809,653, the entire contents of which are incorporated herein by reference, the telemetered system includes a remotely located data receiving device, a sensor for producing signals indicative of a characteristic of a user, and a transmitter device for processing signals received from the sensor and for wirelessly transmitting the processed signals to the remotely located data receiving device. The data receiving device may be a characteristic monitor, a data receiver that provides data to another device, an RF programmer, a medication delivery device (such as an infusion pump), or the like.

Regardless of whether the data receiving device (e.g., a glucose monitor), the transmitter device, and the sensor (e.g., a glucose sensor) communicate wirelessly or via an electrical wire connection, a characteristic monitoring system of the type described above is of practical use only after it has been calibrated based on the unique characteristics of the individual user. According to the current state of the art, the user is required to externally calibrate the sensor. More specifically, and in connection with the illustrative example of a diabetic patient, the latter is required to utilize a finger-stick blood glucose meter reading an average of two-four times per day for the duration that the characteristic monitor system is used. Each time, blood is drawn from the user's finger and analyzed by the blood glucose meter to provide a real-time blood sugar level for the user. The user then inputs this data into the glucose monitor as the user's current blood sugar level which is used to calibrate the glucose monitoring system.

Such external calibrations, however, are disadvantageous for various reasons. For example, blood glucose meters are not perfectly accurate and include inherent margins of error. Moreover, even if completely accurate, blood glucose meters are susceptible to improper use; for example, if the user has handled candy or other sugar-containing substance immediately prior to performing the finger stick, with some of the sugar sticking to the user's fingers, the blood sugar analysis will result in an inaccurate blood sugar level indication. Furthermore, there is a cost, not to mention pain and discomfort, associated with each application of the finger stick.

There is therefore a need for a real-time, self-calibrating sensor that reduces the frequency of, and potentially eliminates the need for, finger sticks.

SUMMARY OF THE DISCLOSURE

According to an embodiment of the invention, a system for calibrating a sensor of a characteristic monitoring system in real time utilizes a self-calibration module for periodic determination of, and compensation for, the IR drop across unwanted resistances in a cell. The self-calibration module includes a first control unit having a potentiostat, a second control unit, and a current-interrupt switch connected between the potentiostat and the sensor's counter electrode. The first control unit uses the potentiostat to ensure that a measured voltage across the sensor's working and reference electrodes (Vmeasured) is substantially equal to an input voltage (Vactual) of the potentiostat. The second control unit aims to ensure that the overpotential (Vimportant) in the cell is substantially equal to an optimally desired voltage across the sensor's working and reference electrodes (Vset), where the "overpotential" may be defined as the effective amount of potential that is not consumed by the unwanted resistances and, as such, drives the electrochemical reaction at the working electrode. In embodiments of the invention, the second control unit may employ a PID controller to calculate Vactual based on Vimportant.

In a particular embodiment of the invention, a method of calibrating the sensor in real time includes obtaining a value for Vmeasured, determining the magnitude of the IR drop, calculating the value of Vimportant by subtracting the magnitude of the IR drop from Vmeasured, and then using the first and second controllers, on a periodic basis, to determine Vactual based on Vset and Vimportant (i.e., the IR-compensated value of Vmeasured). Alternatively, Vimportant may be measured or approximated directly as the value of Vmeasured at the time the current-interrupt switch is opened.

In embodiments of the invention, the IR drop may be measured by using a high-frequency (i.e., in the MHz range) ADC data-acquisition module to pinpoint the value of Vmeasured at the point in time when the current-interrupt switch was opened, and then subtracting this value from Vmeasured for the closed circuit. In an alternative embodiment, the magnitude of the IR drop may be estimated through linear regression of acquired samples of Vmeasured over time, where the samples are acquired at a lower rate. In addition, Vimportant may be optimized by also subtracting (from Vmeasured) the value of the open-circuit voltage (Voc) across the sensor's working and reference electrodes to account for the inherent potential that exists across these electrodes.

The above-described steps may be repeated on a periodic basis, such that the sensor is self-calibrating, without the need for external calibration by the user. The repetition period may coincide, for example, with the delay time between successive samplings of the user characteristic being monitored by the characteristic monitoring system.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 1 is a perspective view illustrating a subcutaneous sensor insertion set, a telemetered characteristic monitor transmitter device, and a data receiving device embodying features of the invention;

FIG. 2 is an enlarged longitudinal vertical section taken generally on the line 2-2 of FIG. 1;

FIG. 3 is an enlarged fragmented sectional view corresponding generally with the encircled region 3 of FIG. 2;

FIG. 4 is an enlarged transverse section taken generally on the line 4-4 of FIG. 2;

DETAILED DESCRIPTION OF THE PREFERRED EMBODIMENTS

Figure 5:
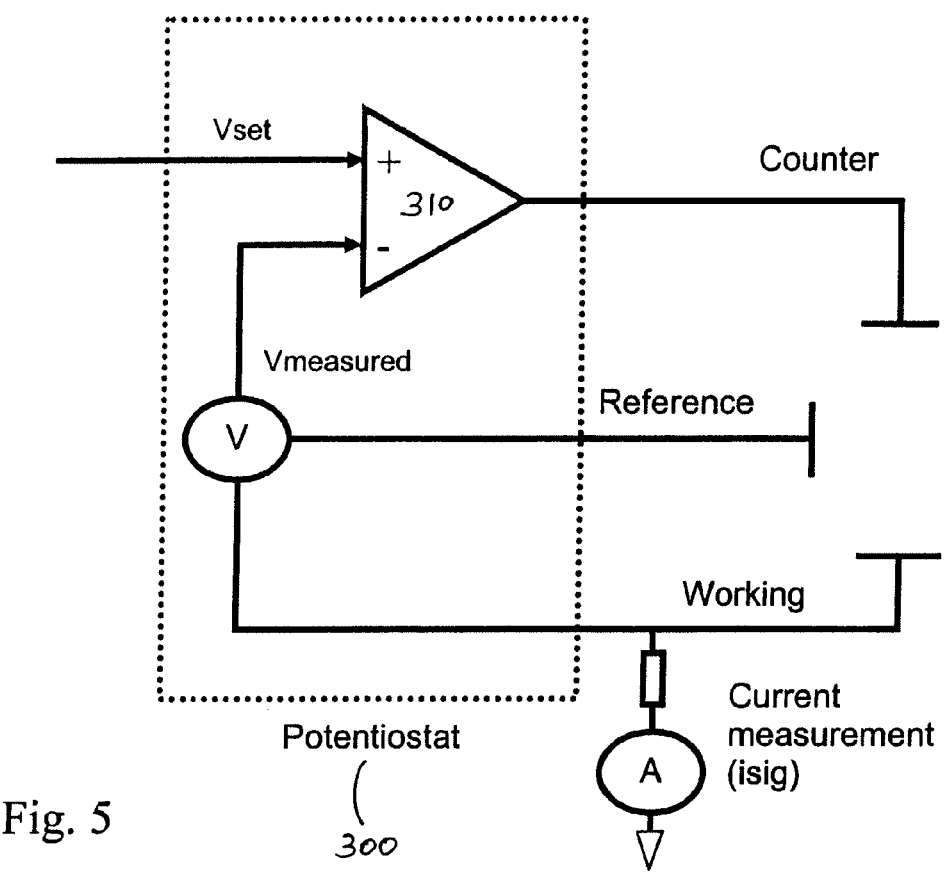
FIG. 5 shows a potentiostat used in implementing a sensor-calibration method according to an embodiment of the invention.

In the following description, reference is made to the accompanying drawings which form a part hereof and which illustrate several embodiments of the present invention. It is understood that other embodiments may be utilized and structural and operational changes may be made without departing from the scope of the present invention.

The present invention is described below with reference to flowchart illustrations of methods, apparatus, and computer program products. It will be understood that each block of the flowchart illustrations, and combinations of blocks in the flowchart illustrations, can be implemented by computer program instructions. These computer program instructions may be loaded onto a computer or other programmable data processing device (such as a controller, microcontroller, or processor) such that the instructions which execute on the computer or other programmable data processing device will implement the functions specified in the flowchart block or blocks. These computer program instructions may also be stored in a computer-readable memory or medium that can direct a computer or other programmable data processing device to function in a particular manner, such that the instructions stored in the computer-readable memory or medium produce an article of manufacture including instructions which implement the function specified in the flowchart block or blocks. The computer program instructions may also be loaded onto a computer or other programmable data processing device to cause a series of operational steps to be performed on the computer or other programmable device to produce a computer-implemented process such that the instructions which execute on the computer or other programmable device provide steps for implementing the functions specified in the flowchart block or blocks presented herein.

As shown in the drawings for purposes of illustration, embodiments of the invention are described for use in conjunction with a telemetered characteristic monitor transmitter that is coupled to a sensor set and transmits data from the sensor set to a characteristic monitor for determining body characteristics. The sensor set may be implanted in and/or through subcutaneous, dermal, sub-dermal, inter-peritoneal or peritoneal tissue. In preferred embodiments of the present invention, the sensor set and monitor are for determining glucose levels in the blood and/or body fluids of the user without the use, or necessity, of a wire or cable connection between the transmitter and the monitor and, in certain embodiments, between the transmitter and sensor set. However, it will be recognized that further embodiments of the invention may be used to determine the levels of other agents, characteristics or compositions, such as hormones, cholesterol, medication concentrations, pH, oxygen saturation, viral loads (e.g., HIV), or the like. The telemetered characteristic monitor system is primarily adapted for use in subcutaneous human tissue. However, still further embodiments may be placed in other types of tissue, such as muscle, lymph, organ tissue, veins, arteries or the like, and used in animal tissue. Embodiments may provide sensor readings on an intermittent or continuous basis.

The telemetered characteristic monitor system 1, in accordance with a preferred embodiment of the present invention includes a percutaneous sensor set 10, a telemetered characteristic monitor transmitter device 100, and a characteristic monitor 200. The percutaneous sensor set 10 utilizes an electrode-type sensor, as described in more detail below. However, in alternative embodiments, the system may use other types of sensors, such as chemical based, optical based, or the like. In further alternative embodiments, the sensor may be of a type that is used on the external surface of the skin or placed below the skin layer of the user. Preferred embodiments of a surface-mounted sensor would utilize interstitial fluid harvested from underneath the skin. The telemetered characteristic monitor transmitter 100 generally includes the capability to transmit data. However, in alternative embodiments, the telemetered characteristic monitor transmitter 100 may include a receiver, or the like, to facilitate two-way communication between the sensor set 10 and the characteristic monitor 200. The characteristic monitor 200 utilizes the transmitted data to determine the characteristic reading. However, in alternative embodiments, the characteristic monitor 200 may be replaced with a data receiver, storage and/or transmitting device for later processing of the transmitted data or programming of the telemetered characteristic monitor transmitter 100. In further embodiments, the telemetered characteristic monitor transmitter 100 transmits to an RF programmer, which acts as a relay, or shuttle, for data transmission between the sensor set 10 and a PC, laptop, Communication-station, a data processor, or the like. Still further embodiments of the telemetered characteristic monitor transmitter 100 may have and use an input port for direct (e.g., wired) connection to a programming or data readout device.

The telemetered characteristic monitor transmitter 100 takes characteristic information, such as glucose data or the like, from the percutaneous sensor set 10 and transmits it via wireless telemetry to the characteristic monitor 200, which displays and logs the received glucose readings. Logged data can be downloaded from the characteristic monitor 200 to a personal computer, laptop, or the like, for detailed data analysis. In further embodiments, the telemetered characteristic monitor system 1 may be used in a hospital environment or the like. The telemetered characteristic monitor transmitter 100 and characteristic monitor 200 may also be combined with other medical devices to combine other patient data through a common data network and telemetry system.

FIG. 1 is a perspective view of a subcutaneous sensor set 10 provided for subcutaneous placement of an active portion of a flexible sensor 12 (see FIG. 2), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In embodiments of the invention, the one or more sensor electrodes 20 may include a counter electrode, a working electrode, and a reference electrode. See, e.g., FIG. 6A. After insertion, the insertion needle 14 is withdrawn to leave the cannula 16 with the sensing portion 18 and the sensor electrodes 20 in place at the selected insertion site.

In preferred embodiments, the subcutaneous sensor set 10 facilitates accurate placement of a flexible thin film electrochemical sensor 12 of the type used for monitoring specific blood parameters representative of a user's condition. Thus, the sensor 12 may monitor glucose levels in the body, and may be used in conjunction with automated or semi-automated medication infusion pumps of the external or implantable type as described in U.S. Pat. Nos. 4,562,751; 4,678,408; 4,685,903; or 4,573,994, to control delivery of insulin to a diabetic patient.

Preferred embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor 200 for monitoring a user's condition in response to signals derived from the sensor electrodes 20. Further description of flexible thin film sensors of this general type may be found in U.S. Pat. No. 5,391,250, entitled METHOD OF FABRICATING THIN FILM SENSORS, which is herein incorporated by reference. The connection portion 24 may be conveniently connected electrically to the monitor 200 or a characteristic monitor transmitter 100 by a connector block 28 (or the like) as shown and described in U.S. Pat. No. 5,482,473, entitled FLEX CIRCUIT CONNECTOR, which is also herein incorporated by reference. Thus, in accordance with embodiments of the present invention, subcutaneous sensor set 10 may be configured or formed to work with either a wired or a wireless characteristic monitor system.

The sensor electrodes 20 may be used in a variety of sensing applications and may be configured in a variety of ways. For example, the sensor electrodes 20 may be used in physiological parameter sensing applications in which a biomolecule is used as a catalytic agent. Thus, the sensor electrodes 20 may be used in a glucose and oxygen sensor having a glucose oxidase enzyme catalyzing a reaction with the sensor electrodes 20. The sensor electrodes 20, along with a biomolecule or some other catalytic agent, may be placed in a human body in a vascular or non-vascular environment. For example, the sensor electrodes 20 and biomolecule may be placed in a vein and subjected to a blood stream, or they may be placed in a subcutaneous or peritoneal region of the human body.

The proximal part of the sensor 12 is mounted in a mounting base 30 adapted for placement onto the skin of a user. As shown, the mounting base 30 is a pad having an underside surface coated with a suitable pressure sensitive adhesive layer 32, with a peel-off paper strip 34 normally provided to cover and protect the adhesive layer 32, until the sensor set 10 is ready for use. As shown in FIGS. 1 and 2, the mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. In preferred embodiments, the adhesive layer 32 includes an anti-bacterial agent to reduce the chance of infection; however, alternative embodiments may omit the agent. In the illustrated embodiment, the mounting base is generally rectangular, but alternative embodiments may be other shapes, such as circular, oval, hour-glass, butterfly, irregular, or the like.

The insertion needle 14 is adapted for slide-fit reception through a needle port 42 formed in the upper base layer 36 and further through the lower bore 40 in the lower base layer 38. As shown, the insertion needle 14 has a sharpened tip 44 and an open slot 46 which extends longitudinally from the tip 44 at the underside of the needle 14 to a position at least within the bore 40 in the lower base layer 36. Above the mounting base 30, the insertion needle 14 may have a full round cross-sectional shape, and may be closed off at a rear end of the needle 14. Further descriptions of the needle 14 and the sensor set 10 are found in U.S. Pat. Nos. 5,586,553 and 5,954,643, which are herein incorporated by reference.

The cannula 16 is best shown in FIGS. 3 and 4, and includes a first portion 48 having partly-circular cross-section to fit within the insertion needle 14 that extends downwardly from the mounting base 30. In alternative embodiments, the first portion 48 may be formed with a solid core, rather than a hollow core. In preferred embodiments, the cannula 16 is constructed from a suitable medical grade plastic or elastomer, such as polytetrafluoroethylene, silicone, or the like. The cannula 16 also defines an open lumen 50 in a second portion 52 for receiving, protecting and guideably supporting the sensing portion 18 of the sensor 12. The cannula 16 has one end fitted into the bore 40 formed in the lower layer 38 of the mounting base 30, and the cannula 16 is secured to the mounting base 30 by a suitable adhesive, ultrasonic welding, snap fit or other selected attachment method. From the mounting base 30, the cannula 16 extends angularly downwardly with the first portion 48 nested within the insertion needle 14, and terminates before the needle tip 44. At least one window 22 is formed in the lumen 50 near the implanted end 54, in general alignment with the sensor electrodes 20, to permit direct electrode exposure to the user's bodily fluid when the sensor 12 is subcutaneously placed. Alternatively, a membrane can cover this area with a porosity that controls rapid diffusion of glucose through the membrane.

As shown in FIGS. 1 and 2, the telemetered characteristic monitor transmitter 100 is coupled to a sensor set 10 by a cable 102 through a connector 104 that is electrically coupled to the connector block 28 of the connector portion 24 of the sensor set 10. In alternative embodiments, the cable 102 may be omitted, and the telemetered characteristic monitor transmitter 100 may include an appropriate connector (not shown) for direct connection to the connector portion 24 of the sensor set 10 or the sensor set 10 may be modified to have the connector portion 24 positioned at a different location, such as, for example, on the top of the sensor set 10 to facilitate placement of the telemetered characteristic monitor transmitter over the subcutaneous sensor set 10. In yet another embodiment, the monitor transmitter 100 may be combined with the sensor set 10 (or sensor 12) as a single unit. In further embodiments, the telemetered characteristic monitor transmitter 100 may omit the cable 102 and connector 104 and is instead optically coupled with an implanted sensor, in the subcutaneous, dermal, sub-dermal, inter-peritoneal or peritoneal tissue, to interrogate the implanted sensor using visible, and/or IR frequencies, either transmitting to, and receiving a signal from, the implanted sensor, or receiving a signal from the implanted sensor. In yet another alternative embodiment, the telemetered characteristic monitor transmitter 100 and the sensor set 10 may communicate wirelessly.

The telemetered characteristic monitor 100 includes a housing 106 that supports a printed circuit board 108, batteries 110, antenna 112, and the cable 102 with the connector 104. In preferred embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In preferred embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use.

The monitor transmitter 100 may include a sensor interface (which connects with the cable 102), processing electronics, and data formatting electronics (not shown). In embodiments of the invention, the sensor interface, the processing electronics, and the data formatting electronics may be formed as separate semiconductor chips. However, alternative embodiments may combine the various semiconductor chips into a single or multiple customized semiconductor chips.

In preferred embodiments, the telemetered characteristic monitor transmitter 100 provides power to the sensor set 10 through the cable 102 and cable connector 104. The power is used to monitor and drive the sensor set 10. The power connection is also used to speed the initialization of the sensor 12, when it is first placed under the skin. The use of an initialization process can reduce the time for sensor 12 stabilization from several hours to an hour or less.

At the completion of the stabilizing process, a reading may be transmitted from the sensor set 10 and the telemetered characteristic monitor transmitter 100 to the characteristic monitor 200, and then the user will input a calibrating glucose reading (e.g., by performing a finger stick) into characteristic monitor 200. In alternative embodiments, a fluid containing a known value of glucose may be injected into the site around the sensor set 10, and then the reading is sent to the characteristic monitor 200 and the user inputs the known concentration value, presses a button (not shown) or otherwise instructs the monitor to calibrate using the known value. During the calibration process, the telemetered characteristic monitor transmitter 100 checks to determine if the sensor set 10 is still connected. If the sensor set 10 is no longer connected, the telemetered characteristic monitor transmitter 100 will abort the stabilization process and sound an alarm (or send a signal to the characteristic monitor 200 to sound an alarm).

The characteristic monitor 200 includes a telemetry receiver, a Telemetry Decoder (TD), and a host micro-controller (Host)—not shown—for communication with the telemetered characteristic monitor transmitter 100. The TD is used to decode a received telemetry signal from the transmitter device and forward the decoded signal to the Host, which may be a microprocessor for data reduction, data storage, user interface, or the like. The telemetry receiver receives the characteristic data (e.g., glucose data) from the telemetered characteristic monitor transmitter, and passes it to the TD for decoding and formatting. After complete receipt of the data by the TD, the data is transferred to the Host for processing, where calibration information, based upon user entered characteristic readings (e.g., finger stick blood glucose readings), is performed to determine the corresponding characteristic level (e.g., glucose level) from measurement in the characteristic data (e.g., glucose data). The Host also provides for storage of historical characteristic data, and can download the data to a personal computer, lap-top, or the like, via a com-station, wireless connection, modem or the like. For example, in certain embodiments, the counter electrode voltage is included in the message from the telemetered characteristic monitor transmitter 100 and is used as a diagnostic signal. The raw current signal values generally range from 0 to 999, which represents sensor electrode current in the range between 0.0 to 99.9 nanoAmperes, and is converted to characteristic values, such as glucose values in the range of 40 to 400 mg/dl. However, in alternative embodiments, larger or smaller ranges may be used. The values are then displayed on the characteristic monitor 200 or stored in data memory for later recall.

In further embodiments of the present invention, the characteristic monitor 200 may be replaced by a different device. For example, in one embodiment, the telemetered characteristic monitor transmitter 100 communicates with an RF programmer (not shown) that is also used to program and obtain data from an infusion pump or the like. The RF programmer may also be used to update and program the transmitter 100, if the transmitter 100 includes a receiver for remote programming, calibration or data receipt. The RF programmer can be used to store data obtained from the sensor 12 and then provide it to either an infusion pump, characteristic monitor, computer or the like for analysis. In further embodiments, the transmitter 100 may transmit the data to a medication delivery device, such as an infusion pump or the like, as part of a closed loop system. This would allow the medication delivery device to compare sensor results with medication delivery data and either sound alarms when appropriate or suggest corrections to the medication delivery regimen. In preferred embodiments, the transmitter 100 would include a transmitter to receive updates or requests for additional sensor data. An example of one type of RF programmer can be found in U.S. Pat. No. 6,554,798, which is herein incorporated by reference.

In use, once the sensor and transmitter have been properly positioned, the user programs the characteristic monitor (or it learns) the identification of the transmitter 100 and verifies proper operation and calibration of the transmitter 100. The characteristic monitor 200 and transmitter 100 then work to transmit and receive sensor data to determine characteristic levels. Thus, once a user attaches a transmitter 100 to a sensor set 10 (or otherwise initiates communication therebetween), the sensor 12 is automatically initialized and readings are periodically transmitted, together with other information, to the characteristic monitor 200.

Once the sensor 12 has been initialized, it must be ensured that the sensor 12, and the overall characteristic monitoring system, remain calibrated. Heretofore, this goal has been achieved via techniques in which a blood glucose meter and multiple blood tests are used to obtain reference glucose values which are then correlated with periodically-acquired glucose monitor data. Examples of such techniques may be found in commonly-assigned U.S. Application Publication No. 2005/0027177 and U.S. Pat. Nos. 6,424,847 and 6,895,263, all of which are herein incorporated by reference. Thus, according to the current state of the art, the user is required to externally calibrate the sensor by utilizing a finger-stick blood glucose meter reading an average of two-four times per day for the duration that the characteristic monitor system is used. As noted previously, there are various disadvantages associated with such a technique.

To address these disadvantages, it has been found that, in sensors of the kind described herein, sensor sensitivity may decrease as a direct result of an increase in additional resistances that tend to build up between the working and reference electrodes. This drift in sensitivity, in turn, has an adverse effect on sensor stability, which necessitates more frequent sensor calibrations. Therefore, in order to more accurately control and measure the voltage across the electrochemical reaction being analyzed with a given sensor, and thereby reduce the necessity and frequency of external calibrations, it is important to remove (i.e., account for) any unwanted potentials which might exist across resistances in the vicinity of the electrodes. Once such unwanted potentials are accounted for, the sensor can be calibrated more accurately, in real time, and with little or no need for continual external calibrations by the user.

Accordingly, in an embodiment of the present invention, a first level of sensor calibration may be implemented with standard potentiostat hardware. As shown in FIG. 5, such a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The voltage between the working and reference electrodes is controlled by providing a current to the counter electrode. Thus, when unwanted resistances cause the potential between the working and reference electrodes (i.e., Vmeasured in FIG. 5) to deviate from Vset, the current supply to the counter electrode is adjusted to return the potential to the set potential, thereby re-calibrating the sensor.

However, although the feed-back system of FIG. 5 addresses the build-up of additional resistances between the working and reference electrodes, it does so indirectly by measuring voltages at the various electrodes, as opposed to accounting more directly for the potential (i.e., IR) drop across any such additional resistances. In addition, the inherent voltage between the working and reference electrodes (i.e., the "open-circuit" voltage) is not accounted for. In short, the system depicted in FIG. 5 allows for a calibration process that is less-than-optimal and, as such, may require that a number of re-calibrations, including external inputs by the user, be performed on a frequent basis.

Figure 6A:
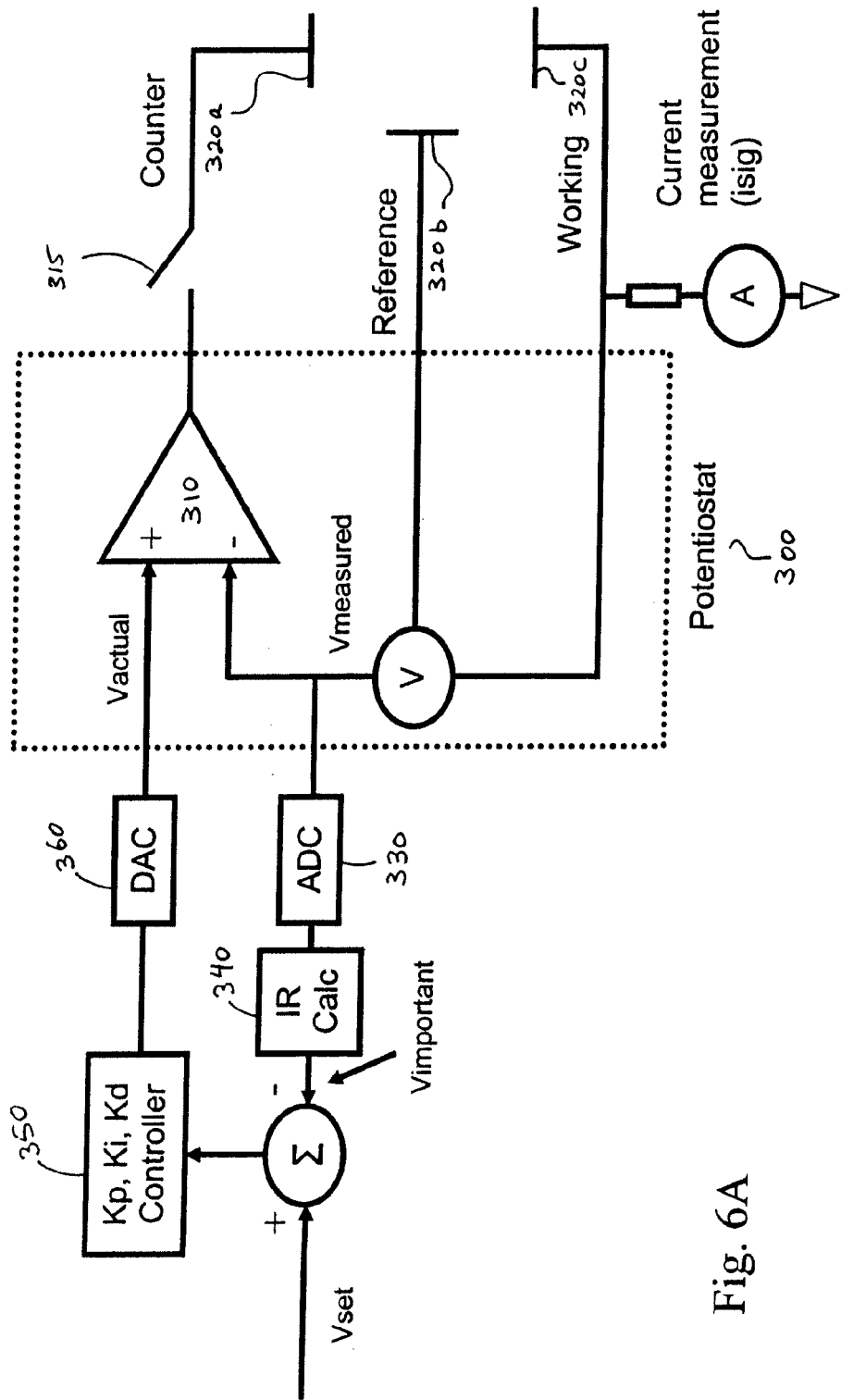
FIG. 6A shows circuitry, components, and modules for implementing a sensor-calibration method according to an embodiment of the invention.

In preferred embodiments of the invention, therefore, real-time self-calibration of the sensor is performed by using an IR compensation technique with a current interrupt. In this regard, FIG. 6A shows a sensor self-calibration module, including an electrical circuit, components, modules, etc., for implementing a self-calibration method according to an embodiment of the present invention. As shown, the self-calibration module includes a potentiostat 300 having an op amp 310. The op amp 310 is connected so as to have two inputs: Vactual and Vmeasured. As shown, Vmeasured is the measured value of the voltage between a working electrode 320c and a reference electrode 320b. The output of the op amp 310 is electrically connected to a counter electrode 320a via a current-interrupt switch 315.

It is known that, when the current in the circuit is interrupted, the voltage at node "V", where values for Vmeasured are obtained, immediately drops by the amount of voltage across the unwanted resistance, i.e., by an amount equal to the IR drop. The magnitude of the IR drop, therefore, may be measured by obtaining the value of Vmeasured while the circuit is still closed, obtaining the value of Vmeasured precisely at the point in time when the current interrupt switch 315 is opened (i.e., t=0), and then subtracting the latter from the former. However, in practical terms, once the switch 315 is opened, it takes Vmeasured on the order of micro-seconds to fall by an amount equal to the magnitude of the IR drop. As such, given the present technological limitations, it is often difficult, if not impossible, to pinpoint time t=0, and then measure a single value for Vmeasured at time t=0.

In light of the above, embodiments of the present invention utilize alternative methods for obtaining the value of Vmeasured at time t=0. With reference to the flow chart of FIG. 7, a real-time self-calibration method according to one embodiment of the present invention is initiated at step 380 with acquiring a sample measurement for Vmeasured while the current interrupt switch 315 is closed. Then, in step 382, with the switch 315 still closed, a sampling sub-routine is started wherein an analog-to-digital converter (ADC) module 330 having a plurality of ADCs is used to obtain a multiplicity of measurements for Vmeasured. In a preferred embodiment, the Vmeasured samples are obtained by said ADCs at a sample rate of about 1 MHz.

After the sampling sub-routine has been initiated, the switch 315 is opened (step 384). The sampling of Vmeasured, however, continues for a period of time after the switch 315 has been opened (step 386). In this way, a multiplicity of successive measurements are obtained for Vmeasured during a pre-determined time period that starts prior to, and ends after, the opening of the switch 315. In a preferred embodiment, the pre-determined time period may be about 100 μsecs, and the time delay between successive ADC measurements may be about 1 μsec. In addition, in a preferred embodiment, the multiplicity of measurements for Vmeasured may be obtained for the range −1.0V≤Vmeasured≤+1.0V.

Figure 6B:
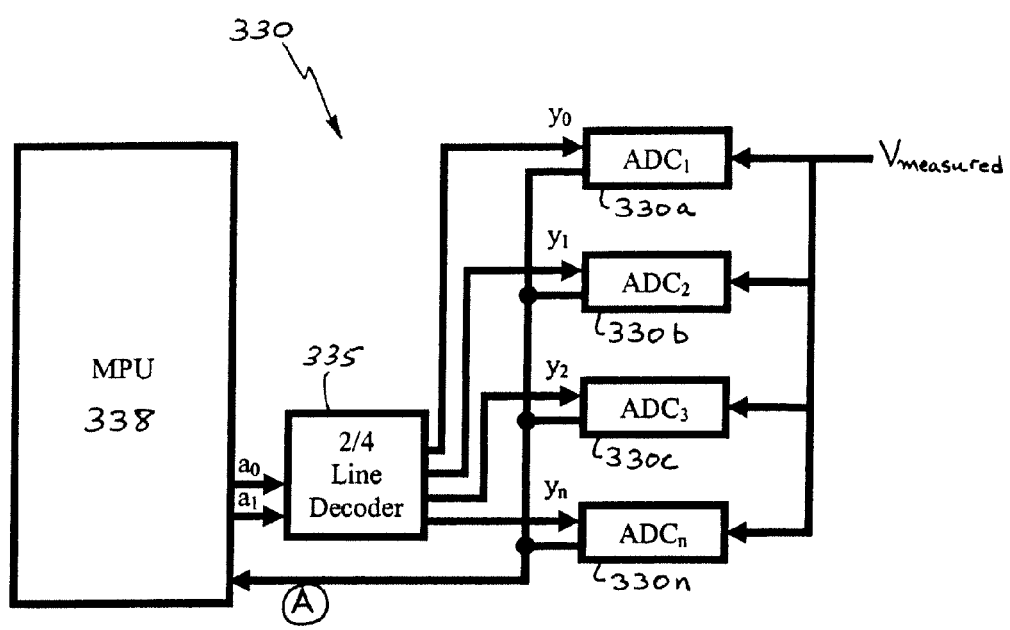
FIG. 6B is block diagram of an ADC data-acquisition module in accordance with an embodiment of the present invention.

FIG. 6B shows, for illustrative purposes, an example of how the multiplicity of Vmeasured samples may be obtained by high-frequency (i.e., in the MHz range) sampling. As shown, a plurality of ADCs 330a-330n are connected in a circuit such that each ADC receives, successively, a respective sampled value for Vmeasured. Thus, when the sampling sub-routine starts, $ADC_1$ may receive the first sample, followed by $ADC_2$ receiving the second sample, $ADC_3$ receiving the third sample, and so on, until each one of the respective Vmeasured samples has been received by a different (succeeding) ADC. Once the sub-routine has ended, a microprocessor unit (MPU) 338 transmits a signal through a line decoder 335 to request the sample obtained by a specific ADC. Thus, for example, a signal with a value of $a_0$-$a_0$ would notify $ADC_1$ that it should transmit its acquired sample to the MPU 338, while a signal with a value of $a_0$-$a_1$ would notify $ADC_2$ to transmit its sample to the MPU 338, etc. It should be noted that, as shown by the line "A" in FIG. 6B, only one ADC at a time may transmit its sample value to the MPU 338.

Once the successive ADC measurements have been processed (sequentially) by the MPU 338, the processed data is searched to locate the sample of Vmeasured that was obtained at t=0 (step 388). With this information, the IR Calculation module 340 can then calculate the magnitude of the IR drop. The latter, however, serves primarily as an intermediate vehicle through which the magnitude of another variable of utmost importance, i.e., Vimportant in FIG. 6A, is determined. As can be deciphered from FIG. 6A, Vimportant is indicative of the voltage that exists across the electrochemical reaction point. That is, in light of the above discussion relating to additional, or unwanted, resistances in the cell, Vimportant is the "over potential" (i.e., the effective amount of potential that is not consumed by the unwanted resistances) that drives the electrochemical reaction at the working electrode 320c. Vimportant, therefore, may be obtained by the relation expressed in Equation 1:

$$V\text{important} = V\text{measured} - IR(\text{Drop}) = V\text{measured}_{t=0}. \quad \text{(Eq. 1)}$$

where $V\text{measured}_{t=0}$ is the value of Vmeasured at current interrupt time=0, and Vmeasured is the sample value obtained at step 380. Thus, at step 390 in FIG. 7, the value of Vimportant is set to be equal to the value obtained by the ADCs for Vmeasured at t=0.

As noted, the block diagram of FIG. 6A shows the circuitry, components, and modules that drive a sensor-calibration module in accordance with embodiments of the present invention (and in conjunction with a sensor of the type shown, e.g., in FIGS. 1 and 2), to implement an IR compensation technique. In the sensor-calibration module shown in FIG. 6A, the potentiostat 300 acts, essentially, as a first control unit (or sub-module) which is operative to ensure that Vmeasured is substantially equal to Vactual, wherein the latter is the second input to the comparator op amp 310.

The sensor-calibration module, however, may also include a second control unit (or sub-module) which is operative to ensure that Vimportant is substantially equal to Vset. Vset is the optimally desired voltage between the working electrode 320c and the reference electrode 320b, and may be pre-determined based on the value of current measurement(s) taken at node "A" in FIG. 6A (see also step 396 in FIG. 7). In the configuration shown in FIG. 6A for illustrative purposes, the second control unit is a proportional-integral-derivative (PID) controller 350. Thus, in this configuration, the IR-compensator portion of the circuit comprises a PID control loop, whereby Vimportant is driven to equal Vset in such a way as to ensure that Vmeasured equals Vactual. To do this, in step 392, Vactual is computed based on Equation 2:

$$V\text{actual} = K_p e + K_d \frac{de}{dt} + K_i \int e \cdot dt \quad \text{(Eq. 2)}$$

where e is the difference between Vset and Vimportant, t is time, $K_p$ is the proportional gain, $K_d$ is the differential gain, and $K_i$ is the integral gain. It is noted that the PID controller may be implemented digitally in software, such that the PID control algorithm may be run on, e.g., a microprocessor within the second control unit. Depending on the specific sensor type and related circuitry, the control algorithm may also be run on the MPU 338, or other computer/processor within the sensor-calibration module. It is also noted that a digital-to-analog converter (DAC) module 360 may be employed to convert the outputted digital signal into an analog input signal to the op amp 310.

Figure 7:
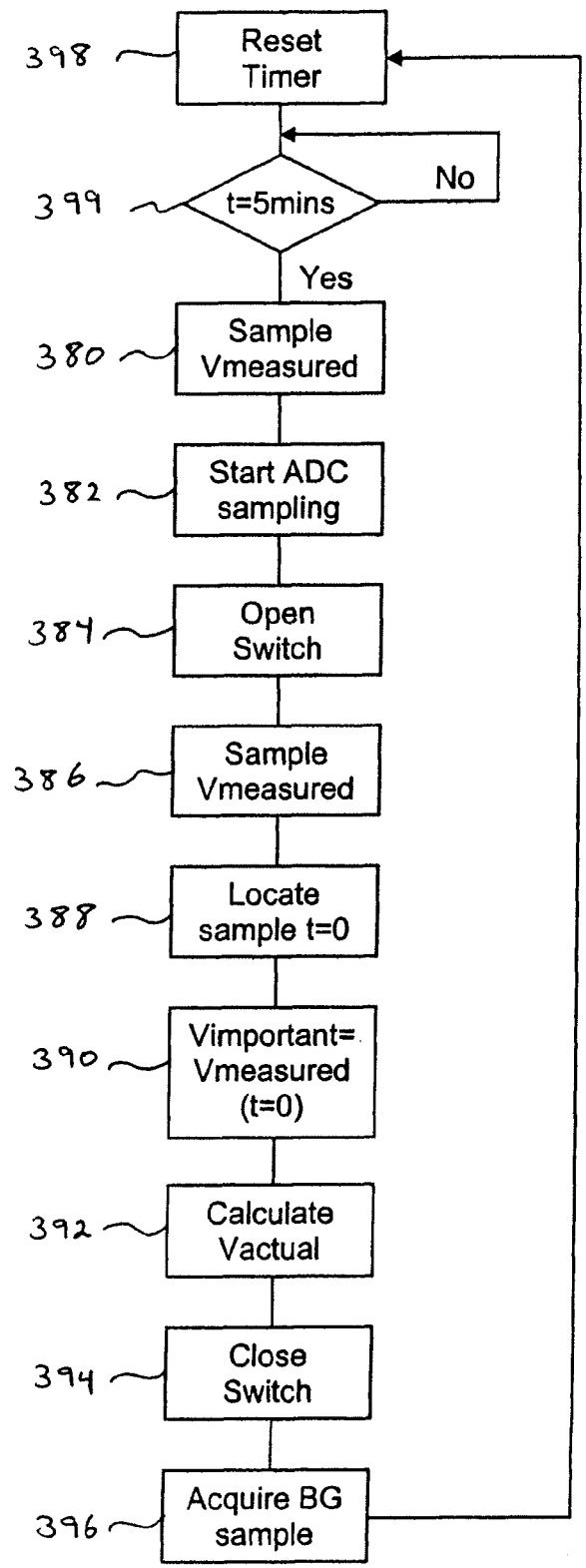
FIG. 7 is a flow chart of the steps taken in implementing a sensor-calibration method according to an embodiment of the invention.

Once Vactual has been calculated, the current interrupt switch 315 is closed (step 394), and the sensor is used to obtain a sample of the user characteristic that is being monitored by the characteristic monitoring system. In FIG. 7, blood glucose (BG) is shown, for purposes of illustration, as the user characteristic of interest. Thus, once the switch 315 has been closed, at step 396, a current measurement is taken at point "A" and converted into a blood glucose level (by using, e.g., a single finger stick to calibrate current measurements for the specific user).

The algorithm then loops back and resets the sensor-calibration module's timer (step 398). Again, with the illustrative example of monitoring blood glucose levels in a user, a typical delay time between successive BG samples may be about five minutes. In a preferred embodiment, it is therefore desirable to have the sensor calibrated at least as frequently as the rate of acquisition of BG samples, and just prior to the BG sample being taken. As such, in one embodiment, once the timer has been reset, a determination is made at step 399 as to whether five minutes have elapsed since the previous calibration of the sensor. If five minutes have passed, then the above-described process is repeated, except that, when step 396 is performed, there is no need for another finger stick, since a correlation between the user's BG level and the sensor's readings has been previously established. If, on the other hand, it is determined at step 399 that less than five minutes have passed since the immediately-previous calibration, the algorithm loops back and re-tries until the elapsed time is equal to five minutes.

As noted previously, Vimportant is indicative of the "over potential" that is available to drive the electrochemical reaction at the working electrode 320c. Thus, the more precise the measurement(s) of Vimportant, the more precise and effective the sensor-calibration process described above. In this regard, it is known that, because they are made of different materials, the working and reference electrodes have an inherent voltage between them. A more precise determination of Vimportant, therefore, would attempt to account for this inherent voltage.

Figure 8:
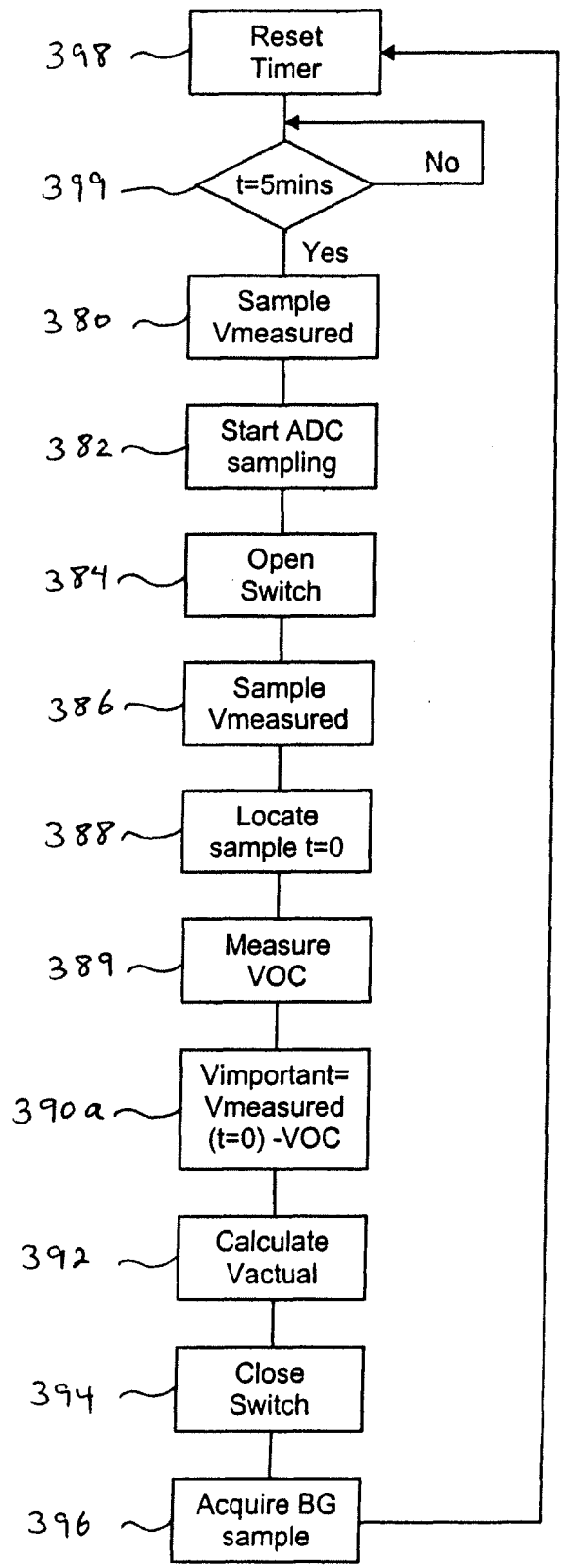
FIG. 8 is a flow chart of the steps taken in implementing a sensor-calibration method according to an alternative embodiment of the invention.

FIG. 8 shows a flow chart that depicts a self-calibration process in accordance with a more preferred embodiment of the invention. As shown, the process includes the same steps 380, 382, 384, 386, and 388 as those described in connection with FIG. 7. However, in this alternative embodiment, in addition to determining the value of Vmeasured at t=0, the inherent voltage noted above is also measured. The inherent voltage is also called the open-circuit voltage (Voc) because its magnitude is obtained by leaving the switch 315 open long enough (e.g., less than 1 msec.) for the voltage between the working electrode 320c and the reference electrode 320b to stabilize to its steady-state, open-circuit value. As this point, Voc is measured (step 389), and Vimportant is calculated in accordance with Equation 3:

$$V\text{important} = V\text{measured} - IR(\text{Drop}) - V\text{oc} = V\text{measured}_{t=0} - V\text{oc}. \quad \text{(Eq. 3)}$$

where, as in Equation 1, $V\text{measured}_{t=0}$ is the value of Vmeasured at current interrupt time=0, and Vmeasured is the sample value obtained at step 380. It is noted that Equation 1 differs from Equation 3 only by the additional term Voc. Once Vimportant has been calculated (step 390a), Vactual is computed in accordance with Equation 2 (step 392), where Vset is now defined as the optimally desired overpotential in the cell. Having the value for Vactual, the same steps 394, 396, 398, and 399 as in FIG. 7 are then followed to calibrate the sensor on a real-time basis.

The real-time, self-calibration techniques for IR compensation depicted in FIGS. 7 and 8 require that a relatively high, uniform sampling rate be used (through the ADC module 330, e.g.) in order to ascertain the value of $V\text{measured}_{t=0}$. However, depending on the specific application, such a sampling rate may be unachievable and/or impractical. As such, in a alternative embodiment of the present invention, the magnitude of the IR drop may be estimated at a lower sampling rate by backwards extrapolation.

Figure 9:
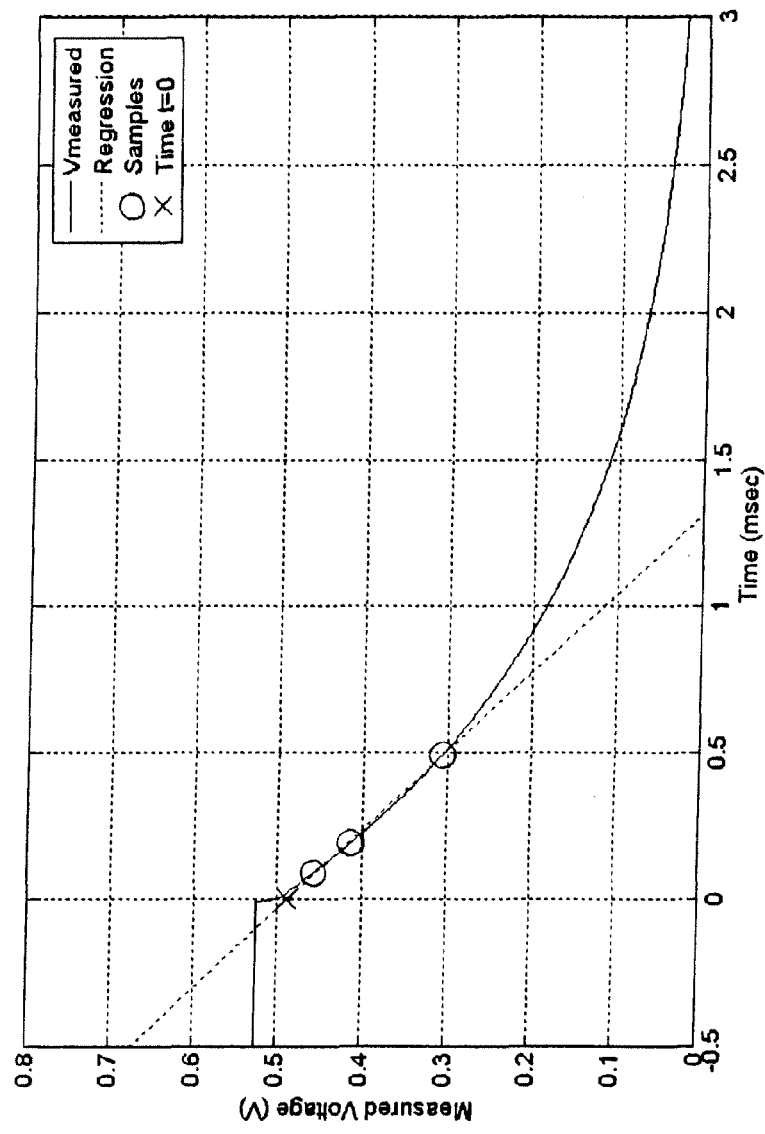
FIG. 9 is a plot diagram showing the exponential decay of a measured voltage over time.

More specifically, in this alternative embodiment, a multiplicity of measurements for Vmeasured are still obtained during a time period that starts prior to, and ends after, the opening of the switch 315. These measurements are then plotted against time. As shown in FIG. 9, the voltage decays in a generally exponential manner. However, experiments have shown that the decay can be approximated as linear for about the first 0.5 milliseconds after the switch has been opened (i.e., until about t≈0.5 msec.). As such, an estimate of the decaying gradient can allow for a backwards-in-time extrapolation (to the point in time when the switch was opened) with generally as few as two or three sample points.

Thus, by way of example, FIG. 9 illustrates the results of an experiment in which samples were acquired at times t≈0.1 msec., t≈0.2 msec., and t≈0.5 msec., and linear regression was performed to backward extrapolate to time t=0 to obtain an approximate value for $V\text{measured}_{t=0}$. As shown in the Vmeasured-vs.-time plot, the exponential decay of Vmeasured can be estimated as linear for approximately the first 0.5 msec., and a regression line generated, such that an estimated value can be obtained for Vmeasured at time t=0.

Figure 10:
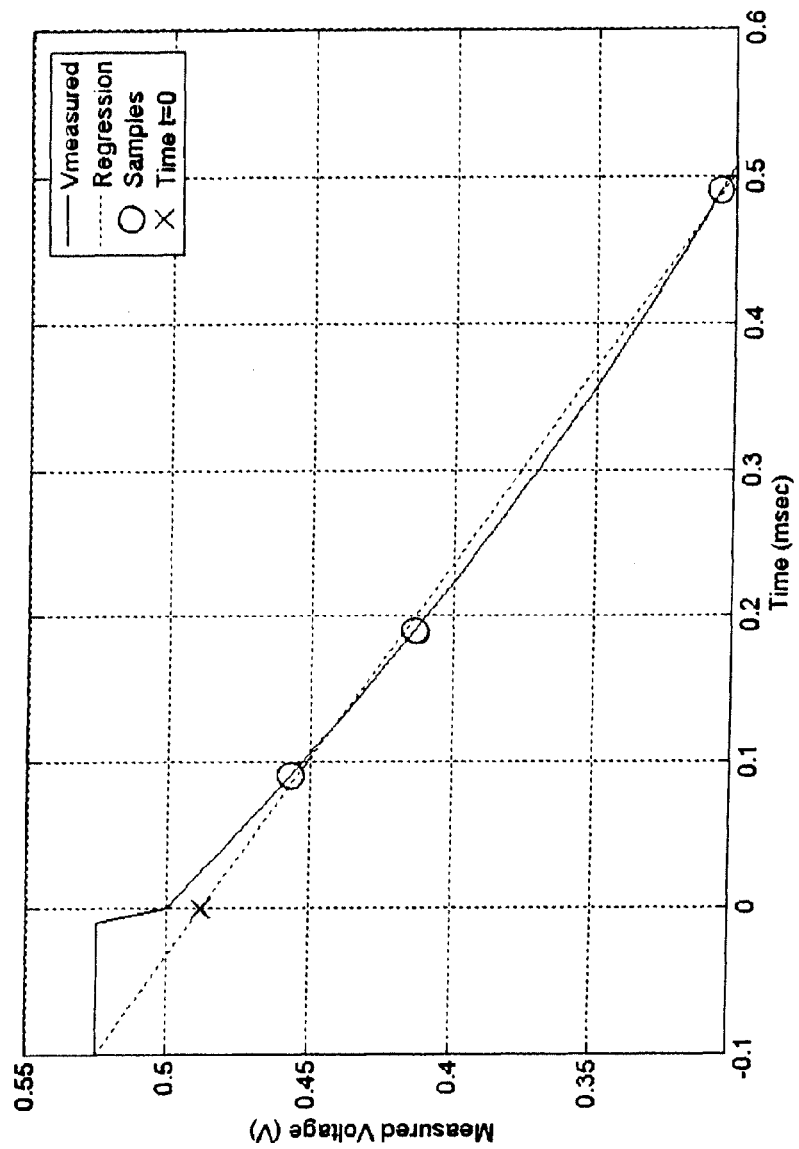
FIG. 10 is an enlarged view of the portion of the plot shown in FIG. 9 that corresponds to $-0.1$ msec.$\leq t \leq +0.6$ msec.

FIG. 10 depicts an enlarged view of the first 0.5 msec. of the Vmeasured-vs.-time plot of FIG. 9. For the purposes of the experiment, a Vmeasured of 0.525V was observed with the current interrupt switch 315 closed. When the switch was opened, Vmeasured dropped to 0.5V before decaying exponentially. Therefore, Vmeasured at time t=0 is 0.5V, with an IR drop of 0.025V. Using backwards-in-time extrapolation, a regression line was then calculated as previously described, which resulted in an estimated $V\text{measured}_{t=0}$ value of 0.49V, with an IR drop of 0.035V. This resulted in a measurement error of approximately 2%, which may, depending on the specific application, prove to be trivial. Of course, once an approximate value for $V\text{measured}_{t=0}$ has been obtained, the remainder of the self-calibration process is carried out as shown in FIGS. 7 and 8.

In yet other alternative embodiments of the invention, the current-interrupt switch 315 may not be necessary at all. Thus, in one such embodiment, the IR drop may be measured by applying AC signals to the cell and analyzing the effect. More specifically, it is known that two resistances exist in series between the working and reference electrodes: The unwanted resistance across which the IR drop is observed, and the faradaic resistance whose potential is equal to Vimportant. In parallel with the faradic resistance is a capacitance that does not exist across the unwanted resistance. With this configuration, high-frequency signals passed between the working and reference electrodes would pass through the above-mentioned capacitance with no voltage drop, such that the capacitance behaves essentially as a short circuit. When, on the other hand, low-frequency signals are applied, the capacitance behaves as an open circuit. Therefore, at high frequencies, where the faradic capacitance is effectively a short circuit, the unwanted resistance would be equal to the applied voltage divided by the cell current. With the unwanted resistance known, the IR drop may be calculated at a later time by multiplying the magnitude of the resistance by the cell current.

It should be noted that the various alternative embodiments of the present invention are not necessarily mutually exclusive, and two or more self-calibration processes may be carried out together, wherein one approach may be used to verify the efficacy of another, or a primary and a secondary approach may be used to provide a redundancy in the system. In addition, one approach, e.g., that depicted in FIG. 7, may be used for control purposes (i.e., for real-time self-calibration of the sensor), while a second approach, e.g., that depicted in FIG. 8, is used for diagnostic purposes (i.e., to check the status of a sensor, where an excessive IR drop, for example, would indicate a sensor malfunction), or vice versa.

In addition, embodiments of the present invention have been described in connection with specific circuit configurations and/or electronic components, modules, sub-modules, etc. However, various alternatives may be used, all of which are intended to be covered by the claims herein. For example, with reference to FIGS. 1 and 2, in a self-calibrating characteristic monitoring system in accordance with embodiments of the invention, the sensor-calibration module (including any microprocessors, controllers, and associated electronics) may be contained within the housing 106 of the transmitter device 100. Alternatively, the sensor-calibration module may be contained within the same housing as that of the sensor 12. In yet a third embodiment, the sensor-calibration module may be contained within the same housing as that of the data receiving device 200. Moreover, the sensor, the transmitter device, and the data receiving device may communicate with one another either through an electrical cable or wirelessly.

Similarly, in various embodiments of the invention described herein, the electronic circuit has included an operational amplifier for measuring and controlling the voltage between the working and reference electrodes. However, any comparator circuit or differential amplifier may be used in place of the op amp. Specifically, low current transistors, such as, e.g., Field effect transistors (FET) and the like may be utilized to perform these functions.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system for calibrating a sensor of a characteristic monitoring system in real time by determining, and compensating for, an IR drop across unwanted resistances in a cell, said sensor including a counter electrode, a reference electrode, and a working electrode in communication with a user's blood or interstitial fluids to produce signals indicative of said characteristic, the system comprising:
    a first control unit having a potentiostat, said potentiostat including an operational amplifier connected in an electrical circuit to maintain substantial equality between the magnitude of a measured voltage across the sensor's working and reference electrodes and the magnitude of an applied voltage;
    a current-interrupt switch electrically connected between the operational amplifier's output and the sensor's counter electrode to provide a closed circuit when the switch is closed and an open circuit when the switch is opened; and
    a second control unit including a microprocessor and connected in the electrical circuit to maintain substantial equality between the magnitude of an optimally desired voltage across the sensor's working and reference electrodes and the magnitude of an effective amount of potential in the cell that drives electrochemical reactions at the working electrode, said effective amount of potential reflecting an adjustment for the magnitude of said IR drop, and said second control unit providing said applied voltage as an input to the operational amplifier,
        wherein the second control unit estimates the magnitude of the IR drop through linear regression of acquired open-circuit samples of said measured voltage across the sensor's working and reference electrodes over time and then calculates the magnitude of said effective amount of potential in the cell by subtracting the magnitude of the IR drop from the closed-circuit magnitude of said measured voltage across the sensor's working and reference electrodes; and
        wherein the magnitude of said effective amount of potential in the cell is optimized by further subtracting therefrom the magnitude of the open-circuit voltage across the sensor's working and reference electrodes.

2. The system of claim 1, wherein the second control unit is a proportional-integral-derivative (PID) controller.

3. The system of claim 2, wherein the PID controller calculates the magnitude of said applied voltage based on the magnitude of said effective amount of potential in the cell.

4. The system of claim 1, further including a transmitter device that is in communication with the sensor to receive signals therefrom, said transmitter device including a processor to process the signals from the sensor and a transmitter for wirelessly transmitting the processed signals to a data receiving device.

5. The system of claim 4, wherein the data receiving device is an insulin pump.

6. The system of claim 4, wherein said system and said data receiving device are contained within a single housing.

7. The system of claim 1, wherein said system and said sensor are contained within a single housing.

8. The system of claim 1, wherein said characteristic is a glucose level in the body of the user.

9. The system of claim 1, wherein the sensor is implantable in tissue selected from the group consisting of subcutaneous, dermal, sub-dermal, intra-peritoneal, and peritoneal tissue.

10. The system of claim 1, wherein the sensor is a percutaneous sensor.

11. A system for calibrating a sensor of a characteristic monitoring system in real time by determining, and compensating for, an IR drop across unwanted resistances in a cell, said sensor including a counter electrode, a reference electrode, and a working electrode in communication with a user's blood or interstitial fluids to produce signals indicative of said characteristic, the system comprising:
    a first control unit having a potentiostat, said potentiostat including an operational amplifier connected in an electrical circuit to maintain substantial equality between the magnitude of a measured voltage across the sensor's working and reference electrodes and the magnitude of an applied voltage;
    a current-interrupt switch electrically connected between the operational amplifier's output and the sensor's counter electrode to provide a closed circuit when the switch is closed and an open circuit when the switch is opened; and
    a second control unit including a microprocessor and connected in the electrical circuit to maintain substantial equality between the magnitude of an optimally desired voltage across the sensor's working and reference electrodes and the magnitude of an effective amount of potential in the cell that drives electrochemical reactions at the working electrode, said effective amount of potential reflecting an adjustment for the magnitude of said IR drop, and said second control unit providing said applied voltage as an input to the operational amplifier,
        wherein the second control unit estimates the magnitude of the IR drop through linear regression of acquired open-circuit samples of said measured voltage across the sensor's working and reference electrodes over time and then calculates the magnitude of said effective amount of potential in the cell by subtracting the magnitude of the IR drop from the closed-circuit magnitude of said measured voltage across the sensor's working and reference electrodes;
        wherein the magnitude of said effective amount of potential in the cell is optimized by further subtracting therefrom the magnitude of the open-circuit voltage across the sensor's working and reference electrodes; and
        wherein the magnitude of said open-circuit voltage is obtained by allowing, while said switch remains open, the voltage between the working and reference electrodes to stabilize to a steady-state value, and then measuring said steady-state value.

12. The system of claim 11, wherein the second control unit is a proportional-integral-derivative (PID) controller.

13. The system of claim 12, wherein the PID controller calculates the magnitude of said applied voltage based on the magnitude of said effective amount of potential in the cell.

14. The system of claim 11, further including a transmitter device that is in communication with the sensor to receive signals therefrom, said transmitter device including a processor to process the signals from the sensor and a transmitter for wirelessly transmitting the processed signals to a data receiving device.

15. The system of claim 14, wherein the data receiving device is an insulin pump.

16. The system of claim 14, wherein said system and said data receiving device are contained within a single housing.

17. The system of claim 11, wherein said system and said sensor are contained within a single housing.

18. The system of claim 11, wherein said characteristic is a glucose level in the body of the user.

19. The system of claim 11, wherein the sensor is implantable in tissue selected from the group consisting of subcutaneous, dermal, sub-dermal, intra-peritoneal, and peritoneal tissue.

20. The system of claim 11, wherein the sensor is a percutaneous sensor.

21. A system for calibrating a sensor of a characteristic monitoring system in real time by determining, and compensating for, an IR drop across unwanted resistances in a cell, said sensor including a counter electrode, a reference electrode, and a working electrode in communication with a user's blood or interstitial fluids to produce signals indicative of said characteristic, the system comprising:
   a first control unit having a potentiostat, said potentiostat including an operational amplifier connected in an electrical circuit to maintain substantial equality between the magnitude of a measured voltage across the sensor's working and reference electrodes and the magnitude of an applied voltage;
   a current-interrupt switch electrically connected between the operational amplifier's output and the sensor's counter electrode to provide a closed circuit when the switch is closed and an open circuit when the switch is opened; and
   a second control unit including a microprocessor and connected in the electrical circuit to maintain substantial equality between the magnitude of an optimally desired voltage across the sensor's working and reference electrodes and the magnitude of an effective amount of potential in the cell that drives electrochemical reactions at the working electrode, said effective amount of potential reflecting an adjustment for the magnitude of said IR drop, and said second control unit providing said applied voltage as an input to the operational amplifier,
      wherein the second control unit estimates the magnitude of the IR drop through linear regression of acquired open-circuit samples of said measured voltage across the sensor's working and reference electrodes over time.

22. The system of claim 21, wherein the magnitude of said open-circuit voltage is obtained by allowing, while said switch remains open, the voltage between the working and reference electrodes to stabilize to a steady-state value, and then measuring said steady-state value.

23. The system of claim 21, wherein the second control unit is a proportional-integral-derivative (PID) controller.

24. The system of claim 23, wherein the PID controller calculates the magnitude of said applied voltage based on the magnitude of said effective amount of potential in the cell.

25. The system of claim 21, further including a transmitter device that is in communication with the sensor to receive signals therefrom, said transmitter device including a processor to process the signals from the sensor and a transmitter for wirelessly transmitting the processed signals to a data receiving device.

26. The system of claim 25, wherein the data receiving device is an insulin pump.

27. The system of claim 25, wherein said system and said data receiving device are contained within a single housing.

28. The system of claim 21, wherein said system and said sensor are contained within a single housing.

29. The system of claim 21, wherein said characteristic is a glucose level in the body of the user.

30. The system of claim 21, wherein the sensor is implantable in tissue selected from the group consisting of subcutaneous, dermal, sub-dermal, intra-peritoneal, and peritoneal tissue.

31. The system of claim 21, wherein the sensor is a percutaneous sensor.

32. A system for calibrating a sensor of a characteristic monitoring system in real time by determining, and compensating for, an IR drop across unwanted resistances in a cell, said sensor including a counter electrode, a reference electrode, and a working electrode in communication with a user's blood or interstitial fluids to produce signals indicative of said characteristic, the system comprising:
   a first control unit having a potentiostat, said potentiostat including an operational amplifier connected in an electrical circuit to maintain substantial equality between the magnitude of a measured voltage across the sensor's working and reference electrodes and the magnitude of an applied voltage;
   a current-interrupt switch electrically connected between the operational amplifier's output and the sensor's counter electrode to provide a closed circuit when the switch is closed and an open circuit when the switch is opened; and
   a second control unit including a microprocessor and connected in the electrical circuit to maintain substantial equality between the magnitude of an optimally desired voltage across the sensor's working and reference electrodes and the magnitude of an effective amount of potential in the cell that drives electrochemical reactions at the working electrode, said effective amount of potential reflecting an adjustment for the magnitude of said IR drop, and said second control unit providing said applied voltage as an input to the operational amplifier,
      wherein the magnitude of said effective amount of potential in the cell is optimized by further subtracting therefrom the magnitude of the open-circuit voltage across the sensor's working and reference electrodes.

33. The system of claim 32, wherein the second control unit estimates the magnitude of the IR drop through linear regression of acquired open-circuit samples of said measured voltage across the sensor's working and reference electrodes over time.

34. The system of claim 32, wherein the magnitude of said open-circuit voltage is obtained by allowing, while said switch remains open, the voltage between the working and reference electrodes to stabilize to a steady-state value, and then measuring said steady-state value.

35. The system of claim 32, wherein the second control unit is a proportional-integral-derivative (PID) controller.

36. The system of claim 35, wherein the PID controller calculates the magnitude of said applied voltage based on the magnitude of said effective amount of potential in the cell.

37. The system of claim 32, further including a transmitter device that is in communication with the sensor to receive signals therefrom, said transmitter device including a processor to process the signals from the sensor and a transmitter for wirelessly transmitting the processed signals to a data receiving device.

38. The system of claim 37, wherein the data receiving device is an insulin pump.

39. The system of claim 37, wherein said system and said data receiving device are contained within a single housing.

40. The system of claim 32, wherein said system and said sensor are contained within a single housing.

41. The system of claim 32, wherein said characteristic is a glucose level in the body of the user.

42. The system of claim 32, wherein the sensor is implantable in tissue selected from the group consisting of subcutaneous, dermal, sub-dermal, intra-peritoneal, and peritoneal tissue.

* * * * *